United States Patent [19]

Lachnit et al.

[11] Patent Number: 5,756,490
[45] Date of Patent: May 26, 1998

[54] PHARMACEUTICAL COMBINATION PREPARATION FOR HORMONAL CONTRACEPTION

[75] Inventors: Ursula Lachnit; Bernd Düsterberg, both of Berlin, Germany; Jürgen Spona, Wein, Australia

[73] Assignee: Schering Aktiengesellschaft, Berlin, Germany

[21] Appl. No.: 718,401

[22] PCT Filed: Mar. 30, 1995

[86] PCT No.: PCT/EP95/01190

§ 371 Date: Dec. 16, 1996

§ 102(e) Date: Dec. 16, 1996

[87] PCT Pub. No.: WO95/26730

PCT Pub. Date: Oct. 12, 1995

[30] Foreign Application Priority Data

Mar. 30, 1994 [DE] Germany ............ 44 11 585.7

[51] Int. Cl.⁶ ................................................ A61K 31/56
[52] U.S. Cl. ................................ 517/170; 514/843
[58] Field of Search ............................ 514/170, 843

[56] References Cited

U.S. PATENT DOCUMENTS

| | | | |
|---|---|---|---|
| 3,502,772 | 3/1970 | Ijzerman | 424/239 |
| 3,639,600 | 2/1972 | Hendrix | 424/242 |
| 4,921,843 | 5/1990 | Pasquale | 514/170 |
| 5,262,408 | 11/1993 | Bergink | 514/182 |
| 5,280,023 | 1/1994 | Ehrlich et al. | 514/177 |

Primary Examiner—Kimberly Jordan
Attorney, Agent, or Firm—Millen, White, Zelano & Branigan, P.C.

[57] ABSTRACT

A pharmaceutical combination preparation with two hormone components that are manufactured physically separately in a packaging unit and that are intended for time-sequential oral administration, which in each case consist of a number of daily dosage units that are placed physically separately and are individually removable in the packaging unit. As a hormonal active ingredient, a first hormone component contains in combination an estrogen preparation and, in at least a dosage that is sufficient to inhibit ovulation, a gestagen preparation, and as a hormonal active ingredient the second hormone component contains only an estrogen preparation. The first hormone component comprises 23 or 24 daily units and the second hormone component comprises 4 to 10 daily units. The total number of hormone daily units is equal to the total number of days of the desired cycle, but at least 28 days in length. This combination preparation is used for female birth control, and allows for an estrogen content that is as low as possible in each individual dosage unit and also has a low total hormone content per administration cycle, with high contraceptive reliability, low incidence of follicular development, and satisfactory cycle control, with reliable avoidance of intracyclic menstrual bleeding as well as of undesirable side-effects.

13 Claims, No Drawings

PHARMACEUTICAL COMBINATION PREPARATION FOR HORMONAL CONTRACEPTION

DESCRIPTION

This invention relates to a pharmaceutical combination preparation with two hormone components which are manufactured physically separately in a packaging unit and are intended for oral administration that is sequential in time and which consist in each case of a number of physically separate and individually removable daily dosage units placed in the packaging unit, whereby as a hormonal active ingredient a first hormone component contains in combination an estrogen preparation and, in a dosage that is sufficient at least to inhibit ovulation, a gestagen preparation in either one-phase or multiple-phase structuring and as a hormonal active ingredient the second hormone component contains only an estrogen preparation, whereby the first hormone component comprises 23 or 24 daily units and the second hormone component comprises 4 to 8 daily units; the daily units of the first hormone component do not contain the combination of a biogenic estrogen and a synthetic estrogen, and the total number of hormone daily units is equal to the total number of days of the desired cycle, but at least 28-days in length, and a corresponding packing that contains this combination preparation.

Oral contraceptives in the form of combination preparations have been known as so-called one-phase preparations since 1960.

These preparations consist of 21 active ingredient-containing dosage units and 7 active ingredient-free tablets or coated tablets. The daily dosage unit consists of an estrogen and a gestagen. In one-phase preparations, the dose of the active substance that is to be administered daily is equally high in each dosage unit. If the dose of the active components that is to be administered daily is different in the individual dosage units in individual sections over the administration cycle, these are so-called multiple-phase preparations. Triquilar® can be cited as an especially well-known representative (DE-A 23 65 103).

The daily gestagen dosage has been continuously reduced through the development of new, more effective gestagens than those contained in the first oral contraceptives. It was also possible to lower, the daily estrogen dosage, although in most cases ethinylestradiol is still contained as an estrogen in hormonal contraceptives.

Because of the development of new, improved oral contraceptives, the following three points were (and are) emphasized:

(1) Contraceptive reliability, (2) good cycle control, i.e., low incidence of intracyclic menstrual bleeding and (3) a minimum of undesirable side-effects are to be ensured.

Contraceptive reliability is mainly provided by the gestagen component. The amount of its daily dosage corresponds in each case to at least the maximum dose that is considered necessary for the gestagen in question to inhibit ovulation. The ethinylestradiol that is used in most cases as an estrogen in combination preparations is supposed to, increase the ovulation-inhibiting effect of the gestagen and mainly to ensure cycle stability. The daily dose in the case of ethinylestradiol administered alone, which must be used to inhibit ovulation, is 100 μg.

Combination preparations with the most recent generation of gestagens are, e.g., the one-phase preparation Femovan (DE-PS 2546062) or Marvelon (DE-OS 2361120). Milvane® can be mentioned (EP-0 148 724) as an example of a multiple-phase preparation whose dosage units contain a gestagen of the most recent generation, namely gestodene. In the case of these three-phase preparations, in most cases 4-6 coated tablets are administered in the first phase, in which each coated-tablet contains an amount of estrogen in a low dose and a gestagen in a low dose. In the second phase of 4-6 coated tablets, each dosage unit contains an estrogen at a dose that is equal or slightly raised, increased to a maximum up to 2-fold, and a gestagen at a dose that is equal or slightly raised, increased to a maximum up to 1.5-fold. In a third phase of 9-11 units, each coated tablet contains an estrogen at a dose that is equal or is further raised, increased to a maximum of 3 times the initial value. Then come 7 pill-free days.

Recently, multiple-phase combination preparations were also proposed which can provide an extended, i.e., up to 24-day, intake of active ingredient-containing dosage units in a 28-day cycle. In this case, the daily gestagen-dosage amount either increases from the first through the second to the third phase (EP-A 0 491 415), or it decreases (EP-A 0 491 438). To complete the 28-day cycle, 4 blank pill days, 4 placebos, or else 4 exclusively gestagen-containing dosage units follow, or in the second case 4 to 7 blank pill days or 4 to 7 placebos follow.

The purpose of the development of new oral contraceptives with a reduced daily hormone dose was to minimize the side- effects that are described in epidemiological studies. Recent epidemiological data point to such a trend toward better compatibility of low-dosed preparations with respect to cardiovascular side-effects. [Thorogood M., Oral Contraceptives and Cardiovascular Disease: An Epidemiologic Overview; Pharmacoepidemiology and Drug Safety, Vol. 2: 3–16 (1993); Gerstman B. B., Piper J. M., Tomita D. K., Ferguson W. J., Stadel B. V., Lundin F. E.; Oral Contraceptive Estrogen Dose and the Risk of Deep Venous Thromboembolic Disease, Am J E Vol. 133, No. 1, 32–36 (1991); Lidegaard O., Oral Contraception and Risk of a Cerebral Thromboembolic Attack: Results of a Case-Control Study: BMJ Vol. 306, 956–63 (1993); Vessey M., Mant D., Smith A., Yeates D., Oral Contraceptives and Venous-Thromboembolism: Findings in a Large Prospective Study; BMJ, Vol. 292, (1986); Mishell D. R., Oral Contraception: Past, Present and Future Perspectives; Int J Fertile, 36 Suppl., 7–18 (1991)].

A correlation between the amount of the daily estrogen dose and the frequency of cardiovascular complications is assumed.

The preparation with the lowest-dosed amount of estrogen at this time is marketed as Mercilon® and contains 20 μg of ethinylestradiol in combination with 150 μg of desogestrel in each daily dosage unit over 21 days, followed by a 7-day pill-free interval. The cycle control of this preparation is somewhat less good than that of preparations with a higher estrogen dose. The observation, confirmed in several studies, of slighter ovarian suppression for the preparation that contains 20 μg of ethinylestradiol represents another clinically important problem. Obviously, for many women this very low estrogen dose can result in the maturation of follicles, as has been detected in ultrasound studies or hormone studies [Lunell N. O., Carlström K., Zador G., Ovulation Inhibition with a Combined Oral Contraceptive Containing 20 μg of Ethinylestradiol and 250 μg of Levonorgestrel; Acta Obstet Gynecol Scand Suppl. 88: 17–21 (1979); Mall-Haefeli M., Werner-Zodrow L. Huber P. R., Klinische Erfahrungen mit Mercilon und Marvelon unter besonderer BerUcksichtigung der Ovar-Funktion [Clinical Experiments with Mercilon and Marvelon with Special Consideration of Ovarian Function]; Geburtsh. und Frauenheilk. [Childbirth and Gynecology], 51, 35–38. Georg Thieme Verlag, Stuttgart-New York (1991); Strobel E., Behandlung mit oralen Kontrazeptiva [Treatment with Oral Contraceptives]; Fortschr. Med. 110 Jg. No. 20 (1992); Letter to Editor, Contraception 45: 519–521 (1992);

Teichmann A. T., Brill K., Can Dose Reduction of Ethinylestradiol in OCs Jeopardize Ovarian Suppression and Cycle Control? Abstract Book, VIIIth World Congress on Human Reproduction, Bali, Indonesia (1993)].

Until recently, a multiple-day break in the intake of coated tablets that contain active ingredients was deemed necessary to trigger withdrawal bleeding and to ensure adequate cycle control.

Other preparations have been described which contain an estrogenic and a gestagenic active ingredient and which generally are administered over 21 days in constant amounts in each individual dosage unit, in which the intake of this dosage unit that contains an estrogenic and gestagenic active ingredient precedes the intake of exclusively estrogen-containing dosage units (Ijzerman, US-A 3,502,772; Pasquale, US-A 4,921,843; Kuhl et al., EP-A 0 499 348). In the case of these preparations, the patient begins taking dosage units that contain only one estrogenic active ingredient, specifically at a dosage that lies below the ovulation-inhibiting dose of the estrogenic component, which can lead to follicular development, either as early as on the first cycle day (Kuhl) or at the earliest on the second cycle day (Pasquale). Follicular development is thought to be responsible for breakthrough ovulations (Chowdhury et al., "Escape" Ovulation in Women Due to the Missing of Low-Dose Combination Oral Contraceptive Pills, Contraception, 22: 241–247, 1980; Molloy B. G. et al., "Missed Pill" Conception: Fact or Fiction? Brit. Med. J. 290, 1474–1475, 1985). Contraceptive protection is thus jeopardized. The risk of pregnancy is therefore high, especially in the case of intake errors below the 20 μg ethinylestradiol preparations.

From DE-PS 43 08 406 (not prepublished), an ovulation-inhibiting agent in the form of a combination preparation for contraception is already known, in which at least one hormone component that contains both estrogen and gestagen is provided, in which the daily units contain both a biogenic estrogen and a synthetic estrogen. This invention does not relate to such preparations.

The object of this invention is to make available a combination preparation with an estrogen content that is as low as possible in each individual dosage unit but also with a low total hormone content per administration cycle, whereby with high contraceptive reliability, an incidence of follicular development that is as low as possible and satisfactory cycle control with reliable avoidance of intracyclic menstrual bleeding such as breakthrough bleeding and "spottings" are to be achieved and undesirable side-effects are to be avoided.

This object is achieved by the provision of the above-indicated two-phase combination preparation.

According to this invention, preferred are combination preparations whose first hormone component comprises 24 daily units and whose second hormone component comprises 4 to 8 daily units.

In the first phase, beginning with the first day of the cycle, a dosage unit that contains an estrogen in combination with a gestagenic component is administered daily over 23 or 24 days. After that is the second phase, in which an estrogen is administered over 5 days or 4 days over the remaining period in the cycle, which also comprises 28 days.

In the preferred case, 24 daily dosage units that contain an estrogen and a gestagen preparation, as well as 4 daily dosage units that contain only an estrogen preparation, are administered.

In this case, the first phase which contains both estrogen and gestagen can also be structured in multiple phases, for example, in three phases, in a way that is familiar to one skilled in the art (in this connection, see, for example, EP-A 0 148 724). Such a preparation is then referred to as a four-phase preparation.

The one-phase structure of the first hormone component is preferred, however.

When the combination preparation according to the invention is taken, the recruitment of the dominant follicle, which in the spontaneous cycle occurs during the first 6 days of the menstrual cycle, is already efficiently suppressed in the first administration cycle. Thus, with the combination preparation of this invention, follicular development can be suppressed as early as in the first intake cycle, and thus breakthrough ovulations can be avoided, thereby increasing contraceptive reliability.

This is of eminent importance mainly in the case of intake errors, namely especially with hormonal contraceptives with low daily ethinylestradiol dose amounts. Since, in the case of 25% of women who take the pill, intake errors (skipping dosage units or extending the interval between the daily intake of two dosage units to more than 24 hours) are known (Finlay I. G., Scott M. B. G.: Patterns of Contraceptive Pill-taking in an Inner City Practice. Br. Med. J. 1986, 293: 601–602), the combination preparation according to the invention, if it is used as an ovulation-inhibiting agent, increases contraceptive reliability. This is true especially in the case of lowest-dosed preparations.

The increase in the number of dosage units above the usual number of 21 days to 23 or 24 days produces an effective shortening of the pill-free interval, in which the selection of follicles occurs with conventional combination preparations as in a normal menstrual cycle, and thus follicular development results and increased endogenic estrogen is formed. These follicles lead to breakthrough ovulations, as already stated above. These breakthrough ovulations occur to an increased extent especially in the case of intake errors.

The subsequent phase, in which dosage units that contain only one estrogenic component as a hormonal active ingredient are administered daily over 4 to 8 days, ensures withdrawal bleeding and produces stimulation of progesterone receptors in the endometrium, thus ensuring in the subsequent administration cycle a reduced rate of intracyclic menstrual bleeding compared with conventional, low-dosed preparations.

According to a preferred embodiment of the invention, the estrogen of the first hormone component is selected from the group of compounds 17β-estradiol, ethinylestradiol and 17β-estradiol valerate and the gestagen is selected from the group of compounds gestodene, levonorgestrel, desogestrel, 3-ketodesogestrel, .

drospironenone, cyproterone acetate, norgestimate and norethisterone and the estrogen of the second hormone component is selected from the group of compounds 17β-estradiol, ethinylestradiol and 17β-estradiol valerate.

According to another preferred variant of this invention, the estrogen of the first hormone component in each daily dosage unit is contained in a dose of 1.0 to 6.0 mg of 17β-estradiol, 0.01 to 0.04 mg of ethinylestradiol, 1.0 to 6.0 mg of 17β-estradiol valerate and the gestagen in each daily dosage unit is contained in a dose of 0.04 to 0.075 mg of gestodene, 0.05 to 0.125 mg of levonorgestrel, 0.06 to 0.15 mg of desogestrel, 0.06 to 0.15 mg of 3-ketodesogestrel, 1.0 to 3.0 mg of drospironenone, 1.0 to 2.0 mg of cyproterone acetate, 0.2 mg to 0.3 mg of norgestimate, 0.35 to 0.75 mg of norethisterone.

As the daily amounts in the daily units of the first hormone component, 0.015 to 0.025 mg is especially preferred for ethinylestradiol, 1.0 to 4.0 mg is especially preferred for 17β-estradiol valerate, and 0.05 to 0.075 mg is especially preferred for gestodene.

The second hormone component contains the estrogen in each daily dosage unit preferably in an amount of 1.0 to 6.0 mg of 17β-estradiol, 0.002 to 0.04 mg of ethinylestradiol, 1.0 to 6.0 mg of 17β-estradiol valerate.

According to an especially preferred embodiment, the second hormone component in each daily dosage unit contains, as estrogen, ethinylestradiol in an amount of 0.01 to 0.025 mg, 17β-estradiol in an amount of 1.0 to 3.0 mg, or 17β-estradiol valerate in an amount of 1.0 to 4.0 mg.

A preparation according to this invention contains a total of preferably 28 hormone daily units.

As an estrogen for both the first and the second hormone component, primarily ethinylestradiol or 17β-estradiol is considered.

Of the above-mentioned gestagens for the first hormone component, gestodene is to be emphasized; also levonorgestrel is preferred.

17β-estradiol, which can be contained as estrogen both in the first and in the second hormone component, is mentioned only as a possible representative of this 17β-estradiol ester; other such homologous esters can also be used as estrogenic components within the scope of this invention.

The following example is used to explain this invention in more detail:

EXAMPLE 1:

| Day | 1 | 2 | 3 | 4 | 5 | 6 | 7 |
|---|---|---|---|---|---|---|---|
| Composition | C | C | C | C | C | C | C |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C or E | E | E | E | E |

Day=Day of the menstrual cycle, day 1 is the first day of bleeding

C=combination of estrogen and gestagen (=first hormone component)

E=estrogen (=second hormone component).

The dosage units are formulated conventionally using estrogen-/gestagen- and exclusively estrogen-containing tablets, pills, coated tablets, etc. of known adjuvants for production.

The number of daily units in the individual phases within the first hormone component in the case of the structure of the combination preparation according to the invention as a four-phase preparation is indicated below:

|  | 1st Phase | 2nd Phase | 3rd Phase | 4th Phase |
|---|---|---|---|---|
| Number of daily units | 4 to 9 C1 | 4 to 9 C2 | 9 to 13 C3 | E = 28 − (C1 + C2 + C3) |

C1, C2, C3=combination gestagen and estrogen within the first hormone component

According to the invention, the estrogen/gestagen dosage ratios in the daily dosage units of the individual phases should lie within the ranges indicated below. In this case, the dosage in the first phase is set as 1, and the dose ranges in the following phases are indicated as multiples of the dosage in the first phase:

|  | 1st Phase | 2nd Phase | 3rd Phase | 4th Phase |
|---|---|---|---|---|
| estrogen | 1 | 1–2 | 0.5–1.5 | 0.5–1 |
| gestagen | 1 | 1–1.5 | 1.5–3 | — |

The composition of a combination preparation according to the invention in four-phase structure can be seen in the example below:

|  | 1st Phase | 2nd Phase | 3rd Phase | 4th Phase |
|---|---|---|---|---|
| Number of daily units | 5 C1 | 7 C2 | 12 C3 | 4 E |
| ethinylestradiol [mg] or | 0.020 | 0.025 | 0.020 | 0.010 |
| 17β-estradiol [mg] and | 2.000 | 3.000 | 2.000 | 1.000 |
| gestodene [mg] or | 0.050 | 0.060 | 0.070 | — |
| levonorgestrel [mg] | 0.050 | 0.075 | 0.100 | — |

The combination preparation according to the invention is used in female contraception by administering the daily dosage units of the first hormone component over 23 or 24 days, beginning on day one of the menstrual cycle (first day of menstrual bleeding), followed by 4 to 8 daily dosage units that contain exclusively one estrogen (E), during a total of at least 28 days in the administration cycle. With this combination preparation, pronounced ovarian suppression without frequent follicle stimulation can be achieved, as well as excellent cycle control in the case of low daily estrogen dosage, low total amounts of estrogen, and low total amounts of hormone per administration cycle.

The advantages of this combination preparation (ovulation- inhibiting agent) according to the invention that is administered over generally 28 days compared to the previously described preparations, especially those with a daily ethinylestradiol dose of less than 30 μg and those with a pill-free interval, can be characterized as follows:

1. A significantly lower frequency of follicular development in the user. This means 'a lower risk of breakthrough ovulation and thus greater contraceptive reliability, especially in the case of intake errors.

2. The recruitment of the dominant follicle is suppressed as early as in the first cycle by extending the intake of the combination to 23 or 24 days.

3. The intake of 4 to 8 daily estrogen dosage units each in connection with the administration of the 23- or 24-day combination dosage results in considerably improved cycle control and a lower incidence of side-effects, such as headaches, within the framework of the premenstrual syndrome.

4. Other clinical symptoms that are attributable to greatly fluctuating endogenic estrogen levels, such as, for example, breast tenseness, are reduced also clearly 0.015 to 0.025 mg owing to the considerably greater ovarian suppression.

The above-mentioned advantages, especially the suppression of follicular development and the accompanying inhibition of endogenic estrogen production, are more pronounced in the case of the combination preparations according to the invention, which comprise 24 daily units of the first hormone component and thus, as mentioned above, the latter are preferred.

The formulation of an estrogen and a gestagen for the production of a combination preparation according to the invention is carried out completely analogously to the way already known for conventional oral contraceptives with a 21-day intake period of the active ingredients, such as, for example, Femovan® (ethinylestradiol/gestodene) or Microgynon® (ethinylestradiol/levonorogestrel). The formulation of the dosage units that contain only estrogen can also be carried out quite analogously to the way known for already obtained estrogen-containing agents that are intended for oral use, for example, Progynon C®.

A packing that contains a combination preparation according to the invention is also built up analogously to packings for already known oral contraceptives that are on the market, with the difference that, instead of the usual 21 dosage units that contain active components, now 23 or 24 such dosage units and another 4 to 8 dosage units that contain only estrogen are present. As a packaging form for the combination preparation according to the invention, generally a conventional blister pack is used, but other packaging forms that are known for this purpose are also conceivable.

In addition, the invention relates to a process for female contraception in which the above-described combination preparation is administered in the indicated way.

To determine equivalent-action amounts of ethinylestradiol and 17β-estradiol, on the one hand, and various gestagens such as gestodene, levonorgestrel, desogestrel and 3-ketodesogestrel, on the other hand, reference is made to the indications given in EP-A-0 253 607. Other details for determining dose equivalents of various gestagenic active ingredients are found in, for example, "Probleme der Dosisfindung: Sexualhormone [Problems of Dose Finding: Sex Hormones]"; F. Neumann et al., in "Arzneimittelforschung [Pharmaceutical Agent Research]" (Drug Research) 27, 2a, 296–318 (1977) as well as in "Aktuelle Entwicklungen in der hormonalen Kontrazeption [Current Developments in Hormonal Contraception]": H. Kuhl in "Gynäkologe [Gynecologist]" 25: 231–240 (1992).

We claim:

1. Pharmaceutical combination preparation with two hormone components that are manufactured physically separately in a packaging unit and that are intended for time-sequential oral administration, which in each case consist of a number of daily dosage units that are placed physically separately and individually removable in the packaging unit, whereby as a hormonal active ingredient a first hormone component contains in combination an estrogen preparation and in at least a dosage that is sufficient to inhibit ovulation a gestagen preparation in either a one-phase or multiple-phase structure and as a hormonal active ingredient the second hormone component contains only an estrogen preparation, whereby the first hormone component comprises 23 or 24 daily units and the second hormone component comprises 4 to 10 daily units, the daily units of the first hormone component do not contain the combination of a biogenic estrogen and a synthetic estrogen, and the total number of hormone daily units is equal to the total number of days of the desired cycle, but at least 28 days in length.

2. Combination preparation according to claim 1, wherein the estrogen of the first hormone component is selected from the group of compounds 17β-estradiol, ethinylestradiol and 17β-estradiol valerate and the gestagen is selected from the group of compounds gestodene, levonorgestrel, desogestrel, 3-ketodesogestrel, drospironenone, cyproterone acetate, norgestimate and norethisterone and the estrogen of the second hormone component is selected from the group of compounds 17β-estradiol, ethinylestradiol and 17β-estradiol valerate.

3. Combination preparation according to claim 2, wherein the estrogen of the first hormone component in each daily dosage unit is contained in a dose of 1.0 to 6.0 mg of 17β-estradiol, 0.015 to 0.025 mg of ethinylestradiol, and 1.0 to 4.0 mg of 17β-estradiol valerate and the gestagen in each daily dosage unit is contained in a dose of 0.05 to 0.075 mg of gestodene, 0.05 to 0.125 mg of levonorgestrel, 0.06 to 0.15 mg of desogestrel, 0.06 to 0.15 mg of 3-ketodesogestrel, 1.0 to 3.0 mg of drospironenone, 1.0 to 2.0 mg of cyproterone acetate, 0.2 mg to 0.3 mg of norgestimate and 0.35 to 0.75 mg of norethisterone.

4. The combination preparation of claim 3, wherein the second hormone component contains, in each daily dosage unit, an amount of:

1.0 to 6.0 mg of 17β-estradiol, 0.002 to 0.04 mg of ethinylestradiol, and 1.0 to 4.0 mg of 17β-estradiol valerate.

5. Combination preparation according to claim 2, wherein the second hormone component contains, in each daily dosage unit, an amount of 1.0 to 6.0 mg of 17β-estradiol, 0.002 to 0.04 mg of ethinylestradiol, and 1.0 to 4.0 mg of 17β-estradiol valerate.

6. Combination preparation according to claim 5, wherein the second hormone component in each daily dosage unit contains ethinylestradiol in an amount of 0.01 to 0.025 mg.

7. The combination preparation of claim 2, wherein the second hormone component contains, in each daily dosage unit, an amount of:

1.0 to 3.0 mg of 17β-estradiol, 0.01 to 0.025 mg of ethinylestradiol, and 1.0 to 4.0 mg of 17β-estradiol valerate.

8. Combination preparation according to claim 1, wherein the total number of hormone daily units is 28.

9. The combination preparation according to claim 1, wherein the first hormone component has 24 daily units and the second hormone component has 4-8 daily units.

10. The combination preparation according to claim 1, wherein the first hormone component has 24 daily units and the second hormone component has 4 daily units.

11. The combination preparation of claim 1, wherein the estrogen in both the first and second hormone components is selected from ethinylestradiol or 17β-estradiol.

12. The combination preparation of claim 1, wherein the gestagen in the first hormone component is selected from gestodene or levonorgestel.

13. The combination preparation of claim 1, wherein the first hormone component has three phases of daily units wherein the estrogen and/or the gestagen amounts differ between phases.

* * * * *